United States Patent
Graetz et al.

[11] Patent Number: 5,881,724
[45] Date of Patent: Mar. 16, 1999

[54] METHOD AND DEVICE FOR CONTROLLING A RESPIRATOR FOR THERAPEUTIC TREATMENT OF SLEEP APNEA

[75] Inventors: Bernd Graetz, Schenefeld; Jörg Maurer, Oststeinbek, both of Germany

[73] Assignee: Gottlieb Seinmann Geräte für Medizin und Arbeitsschutz GmbH + Co., Hamburg, Germany

[21] Appl. No.: 902,986

[22] Filed: Jul. 30, 1997

[51] Int. Cl.⁶ .................................................. A61M 16/00
[52] U.S. Cl. ................. 128/204.23; 128/204.21; 128/204.22
[58] Field of Search .......... 128/204.18, 204.21, 128/204.22, 204.23, 204.26; 600/532

[56] References Cited

U.S. PATENT DOCUMENTS

| | | |
|---|---|---|
| 3,961,627 | 6/1976 | Ernst et al. ........................ 128/204.21 |
| 5,551,419 | 9/1996 | Froehlich et al. ................. 128/204.23 |
| 5,617,846 | 4/1997 | Graetz et al. . |
| 5,794,614 | 8/1998 | Gruenke et al. .................. 128/204.21 |

FOREIGN PATENT DOCUMENTS 0705615  4/1996  European Pat. Off. .

*Primary Examiner*—Kimberly L. Asher
*Attorney, Agent, or Firm*—Robert W. Becker & Associates

[57] ABSTRACT

A method of controlling a respirator for therapeutic treatment of sleep apnea includes the step of continuously measuring a) a phase angle of a time difference between respiratory flow and respiratory pressure of a patient and b) a pressure amplitude of the patient. The individual respiratory resistance is determined based on the measured pressure amplitude by oscilloresistometry. The respiratory gas pressure is controlled based on the phase angle, the pressure amplitude, and the respiratory resistance. Significant changes of the phase angle are filtered from the signal of the phase angle. A control signal is produced based on the significant changes for controlling the respiratory gas pressure.

10 Claims, 1 Drawing Sheet

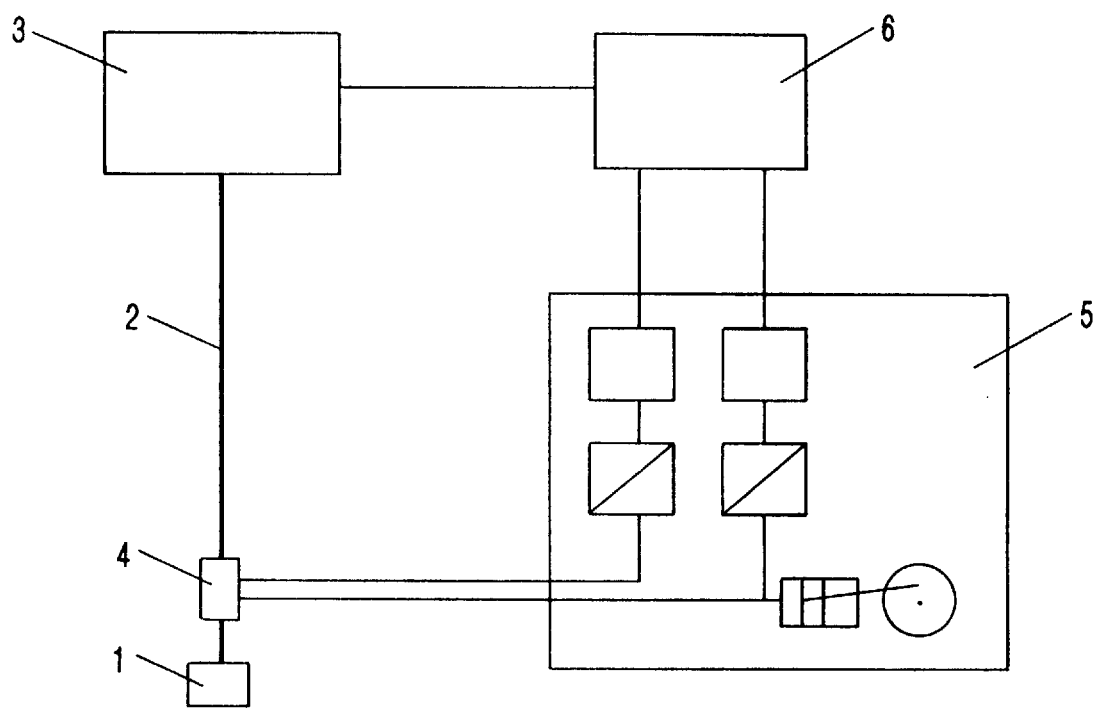

METHOD AND DEVICE FOR CONTROLLING A RESPIRATOR FOR THERAPEUTIC TREATMENT OF SLEEP APNEA

BACKGROUND OF THE INVENTION

The present invention relates to a method for controlling a respirator for therapeutic treatment of sleep apnea as well as to a respirator for performing the inventive method, whereby the phase angle (time difference between respiratory flow and respiratory pressure) and the pressure amplitude correlated to the respiratory resistance are measured as well as the individual respiratory resistance (base value) of the pressure amplitude of a patient with the aid of oscilloresistometry and the respiratory gas pressure is controlled as a function of these values.

Such a device is, for example, known from U.S. Pat. No. 5,617,846.

A considerable number of people suffer from sleeping disorders which affect their daily well-being and their social and professional capabilities as well as their quality of life. Such sleeping disorders include obstructive sleep apnea in which, due to a reduction of the muscle tone, the upper respiratory path ways partly or entirely collapse. The condition primarily treated by the so-called CPAP therapy (CPAP=Continuous Positive Airway Pressure). This is achieved by supplying the patient during the sleeping hours with an air stream of a respiratory gas through a nasal mask. This mask is connected with a hose to the respirator that includes a fan which produces a gas stream with pressure that can be adjusted to be between 5 and 20 mbar above ambient pressure. The gas flow is supplied to the patient with constant pressure or, for facilitating breathing of the patient, is lowered during exhaling to a reduced pressure level. Even though sleep apnea phases occur only for very short periods of time and occupy only a minimal portion of the sleeping hours, the fan in this method operates continuously, i.e., during the entire sleeping hours (night). This reduces acceptance by the patient for such treatment. In order to eliminate these disadvantages, a method for controlling a respirator as well as a respiratory device for performing this method are know from European Patent Application 0 705 615. By oscilloresistometry (oscillatory resistance measurement= ORM) changes in the phase angle of the oscillating pressure amplitude, which is proportional to the respiratory resistance of the patient, are continuously measured whereby after determination of the individual respiratory resistance value (base value of the pressure amplitude) a respiratory gas is supplied under pressure to the patient when deviations from this value are detected. The gas supply is terminated as soon as the base value has been reached again or is at least approximately reached. The dynamics of such a method are determined by the time which elapses from the point of detecting the resistance increase (increase of the pressure amplitude) until the therapeutically effective CPAP pressure has been reached. Within this time window, i.e., even before reaching the therapeutically effective CPAP pressure, sleep apnea may occur.

It is therefore an object of the present invention to improve the sensitivity of the control method by shortening the response time.

SUMMARY OF THE INVENTION

The method of controlling a respirator for therapeutic treatment of sleep apnea according to the present invention is primarily characterized by the following steps:

continuously measuring a) a phase angle of a time difference between respiratory flow and respiratory pressure of a patient and b) a pressure amplitude of the patient;

determining by oscillorresistometry the individual respiratory resistance based on the measured pressure amplitude;

controlling the respiratory gas pressure based on the phase angle, the pressure amplitude, and the respiratory resistance;

filtering significant changes of the phase angle from the signal of the phase angle;

generating a control signal based on the significant changes for controlling the respiratory gas pressure.

The method further comprises the steps of superimposing a sine pressure flow onto the respiratory flow of the patient and simultaneously measuring a pressure course over time of the respiratory gas flow and the superimposed sign pressure flow for determining the oscillatory pressure amplitude that correlates to the respiratory resistance of the patient and the phase angle. The proportion of the superimposed oscillations is filter out of the signal.

Advantageously, changes of the phase angle are filter out of the phase angle signal by FFT (Fast Fourier Transformation).

The changes of the phase angle may be filtered by auto-correlation analysis out of the phase angle signal.

It is also possible to filter out the changes of the phase angle by the method of cluster analysis.

Advantageously, the changes of the phase angle are filtered by a combined method of auto-correlation analysis and median analysis from the phase angle signal.

The present invention also relates to a respirator comprising a respiratory mask, a respiratory gas source connected to the respiratory mask, and a device for continuously measuring a) a phase angle of a time difference between respiratory flow and respiratory pressure of a patient and b) a pressure amplitude of the patient and for determining by oscilloresistometry the individual respiratory resistance of the patient. The respirator furthermore comprises a device for controlling the pressure of the respiratory gas source supplied to the respiratory mask based on significant changes of the phase angle filtered from the signal of the phase angle such that respiratory gas of an optimal respiratory pressure is supplied to the patient.

Advantageously, the respiratory gas source is a fan.

The respirator may further comprise an adjustable pressure control member for adjusting the respiratory gas pressure based on the patient's needs.

The respirator may further comprise a valve-free diaphragm pump for superimposing a sine pressure flow onto the respiratory flow of the patient.

According to the present invention, significant changes (phase jumps) of the phase angle are preferably filtered out of the angle signal by the FFT method (Fast Fourier Transformation), auto-correlation, cluster analysis, or median analysis, and a control signal for pressure adjustment of the respirator is generated therefrom.

With the inventive method for controlling the respirator for therapeutic treatment of sleep apnea patients, the respirator is already activated, i.e., respiratory gas is already supplied to the patient, when the breathing activity of the patient is interrupted by the onsetting sleep apnea which causes significant changes (phase jumps) of the phase angle before effects on the respiratory resistance can be detected. A disruption of the breathing activity of the patient is accompanied by changes of the respiratory pressure and the respiratory flow of the patient. This pressure and flow are determined, without impairing the well-being of the patient, in a simple manner reliably and reproducible with the oscillatory pressure amplitude, and the phase angle is determined therefrom. Distinctive changes of the phase angle, for example, a phase jump by changes of the compliance of the airways, do occur already within a time period before significant changes of the respiratory pressure and respiratory flow can be detected and can thus provide a control value for a timely activation or deactivation of the therapeutic device so that a low supply of oxygen to the patient will not occur and a relief for the patient is achieved because the pressure adjustment of the air-ways is performed early and a soft transition to the respective respiratory gas pressure can be performed.

In an exemplary embodiment of the control method according to the invention, a sine pressure flow is superimposed onto the respiratory flow of a patient. This sine pressure flow is generated by a valve-free diaphragm pump. For determining the oscillatory pressure amplitude, which corresponds to the respiratory resistance of the patient, the pressure course over time within the nasal mask, via which the patient is supplied with respiratory gas, for example, by the blower of a respirator, is measured and the proportion of the superimposed oscillations are filtered out. At the same time, the pressure course within the diaphragm pump is detected. From the time difference between the two pressure signals, the phase angle is determined. Its course has distinctive changes such as phase jumps immediately before the onset of an apnea attack, which most likely are caused by changes of the airway compliance. These significant changes, occurring before the onset of apnea or breathing irregularities, are detected by FFT (Fast Fourier Transformation), auto-correlation, cluster analysis or median analysis and are used to effect a pressure increase within the flow of the supplied respiratory gas, for example, by increasing the rpm of the blower of the respirator. With the oscillating pressure signal, which is proportional to the respiratory resistance of the patient, not only the pressure increase is checked but also the pressure of the respiratory gas is controlled.

A respirator for performing the inventive method is comprised of a respiratory gas source connected to a breathing or respiratory mask whereby the respiratory gas source is inventively embodied as a fan or blower. The respirator further comprises a device for continuously measuring the phase angle (the time difference between respiratory flow and respiratory pressure) and the pressure amplitude correlated to the respiratory resistance as well as for determining the individual respiratory resistance values of a patient according to the ORM principle and is characterized in a control device which with the significant changes (phase jumps) of the phase angle filtered from the signal of the phase angle activates or controls the respiratory gas source such that the patient is supplied with respiratory gas of an optimal, i.e., therapeutically effective pressure.

In a further expedient embodiment of the invention the respirator can be provided with a control member for controlling the pressure of the respiratory gas supply to the patient according to his needs, so that the acceptance of the therapeutic device is improved because the patient can be supplied with a constant pressure comfortable to him when the oscillating pressure amplitude and/or phase angle of the pressure amplitude and/or the respiratory flow of the patient matches the base value or base values.

BRIEF DESCRIPTION OF THE DRAWING

The object and advantages of the present invention will appear more clearly from the following specification in conjunction with the only drawing showing an exemplary embodiment of the inventive respirator in a schematic representation.

DESCRIPTION OF PREFERRED EMBODIMENTS

The respirator for therapeutic treatment of sleep apnea comprises a respiratory mask 1 to be arranged on the nose of a patient. The mask 1 is connected by a breathing hose 2 to a respiratory gas source 3 that is embodied as a fan or blower. Within the breathing hose 2 upstream of the respiratory mask 1, sensors 4 of a device 5 for producing, measuring, and filtering the oscillatory pressure amplitude according to the ORM principle as well as determining the phase angle are provided A control device 6 is connected to the device 5 and can be adjusted to the individual base values of the patient's respiratory resistance with regard to the correlated oscillating pressure amplitude. The respiratory gas source 3 is activated such that respiratory gas is supplied to the patient when significant changes of the phase angle occur. The device 5 comprises a valve-free diaphragm pump (not shown) with which the respiratory flow of the patient can be superimposed by a sine-shaped pressure flow.

The present invention is, of course, in no way restricted to the specific disclosure of the specification and drawings, but also encompasses any modifications within the scope of the appended claims.

What is claimed is:

1. A method of controlling a respirator for therapeutic treatment of sleep apnea, said method comprising the steps of:
   continuously measuring a) a phase angle of a time difference between respiratory flow and respiratory pressure of a patient and b) a pressure amplitude of the patient;
   determining by oscilloresistometry the individual respiratory resistance based on the measured pressure amplitude;
   controlling the respiratory gas pressure based on the phase angle, the pressure amplitude, and the respiratory resistance;
   filtering significant changes of the phase angle from the signal of the phase angle;
   generating a control signal based on the significant changes for controlling the respiratory gas pressure.

2. A method according to claim 1, further comprising the steps of:
   superimposing a sine pressure flow onto the respiratory flow of the patient;
   simultaneously measuring a pressure course over time of the respiratory gas flow and the superimposed sine pressure flow for determining the oscillatory pressure amplitude, that correlates to the respiratory resistance of the patient, and the phase angle; and
   filtering out the proportion of superimposed oscillations.

3. A method according to claim 1, wherein changes of the phase angle are filtered by FFT out of the phase angle signal.

4. A method according to claim 1, wherein changes of the phase angle are filtered by auto-correlation analysis out of the phase angle signal.

5. A method according to claim 1, wherein changes of the phase angle are filtered by the method of cluster analysis out of the phase angle signal.

6. A method according to claim 1, wherein changes of the phase angle are filtered by a combined method of auto-correlation analysis and median analysis out of the phase angle signal.

7. A respirator comprising:

a respiratory mask;

a respiratory gas source connected to said respiratory mask;

a device for continuously measuring a) a phase angle of a time difference between respiratory flow and respiratory pressure of a patient and b) a pressure amplitude of the patient and for determining by oscilloresistometry the individual respiratory resistance of the patient;

a device for controlling the pressure of said respiratory gas source supplied to said respiratory mask based on significant changes of the phase angle filtered from the signal of the phase angle such that respiratory gas of an optimal respiratory pressure is supplied to the patient.

8. A respirator according to claim 7, wherein said respiratory gas source is a fan.

9. A respirator according to claim 7, comprising an adjustable pressure control member for adjusting a respiratory gas pressure based on the patient's needs.

10. A respirator according to claim 7, comprising a valve-free diaphragm pump for superimposing a sine pressure flow onto the respiratory flow of the patient.

* * * * *

UNITED STATES PATENT AND TRADEMARK OFFICE
CERTIFICATE OF CORRECTION

PATENT NO. : 5,881,724
DATED : 3/16/99
INVENTOR(S) : Bernd Graetz and Jörg Maurer It is certified that error appears in the above-indentified patent and that said Letters Patent is hereby corrected as shown below:

On the title page, insert item [30]
[30] Foreign Application Priority Data

July 30, 1996  [DE]  Germany..........296 13 169.5

Signed and Sealed this

Eleventh Day of January, 2000

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,881,724
DATED : March 16, 1999
INVENTOR(S) : Bernd Graetz and Jörg Maurer It is certified that error appears in the above-identified patent and that said Letters Patent is hereby corrected as shown below:

<u>Title page,</u>
The following item should read as follows:

[73] Assignee

Gottlieb Weinmann Geräte für Medizin and Arbeitsschutz GmbH & Co.

Signed and Sealed this

Thirty-first Day of July, 2001

*Attest:*

*Attesting Officer*

NICHOLAS P. GODICI
*Acting Director of the United States Patent and Trademark Office*